(12) United States Patent
Hwang (10) Patent No.: US 8,066,679 B2
(45) Date of Patent: Nov. 29, 2011

(54) SINGLE-HANDEDLY ACTUATABLE SHIELD (75) Inventor: Charles G. Hwang, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 361 days.

(21) Appl. No.: 12/249,259

(22) Filed: Oct. 10, 2008

(65) Prior Publication Data
US 2009/0093771 A1 Apr. 9, 2009

Related U.S. Application Data

(63) Continuation of application No. 11/263,025, filed on Oct. 31, 2005, now abandoned.

(51) Int. Cl.
*A61M 5/32* (2006.01)
(52) U.S. Cl. ......................................... 604/198; 604/192
(58) Field of Classification Search .................. 604/110, 604/192–198, 288.01, 288.04, 187, 82, 201, 604/191, 86, 523, 263; D24/130
See application file for complete search history.

(56) References Cited

U.S. PATENT DOCUMENTS

| | | | |
|---|---|---|---|
| 4,735,618 A | 4/1988 | Hagen | |
| 4,886,503 A | 12/1989 | Miller | |
| 5,348,544 A * | 9/1994 | Sweeney et al. | 604/192 |
| 5,738,655 A | 4/1998 | Vellulunga | |
| 5,738,827 A | 4/1998 | Marquiss | |
| 5,814,018 A * | 9/1998 | Elson et al. | 604/110 |
| 5,910,130 A | 6/1999 | Caizza et al. | |
| 6,280,420 B1 * | 8/2001 | Ferguson et al. | 604/198 |
| 6,592,556 B1 | 7/2003 | Thorne | |
| 7,001,363 B2 * | 2/2006 | Ferguson et al. | 604/198 |
| 2003/0191438 A1 * | 10/2003 | Ferguson et al. | 604/198 |
| 2003/0229317 A1 | 12/2003 | Ferguson et al. | |
| 2004/0220532 A1 * | 11/2004 | Caizza | 604/264 |
| 2005/0059936 A1 | 3/2005 | Fiser et al. | |

FOREIGN PATENT DOCUMENTS

| | | |
|---|---|---|
| EP | 1437153 | 7/2004 |
| GB | 2369779 | 6/2002 |
| WO | WO-01/32241 | 5/2001 |

OTHER PUBLICATIONS

PCT International Search Report in PCT/US2006/040779, mailed Feb. 27, 2007, 3 pgs.

* cited by examiner

*Primary Examiner* — Kevin C Sirmons
*Assistant Examiner* — Andrew Gilbert
(74) *Attorney, Agent, or Firm* — Jeanne P. Lukasavage; Diehl Servilla LLC (57) ABSTRACT

A needle shield is provided for a medical device having a needle cannula. The needle shield includes a guard that is slidably movable along the needle cannula from a proximal position where the tip of the needle cannula is exposed to a distal position where the tip of the needle cannula is shielded. A hinged arm connects the guard to the proximal end of the needle cannula. The hinged arm can be collapsed upon itself, such that the guard is adjacent to the proximal end of the needle cannula. The hinged arm can be extended to cause the guard to move distally along the needle cannula and into a position for shielding the tip of the needle cannula. Structure is provided to prevent excessive additional rotation of the hinged elements of the hinged guard after the tip of the needle cannula is shielded.

27 Claims, 12 Drawing Sheets

SINGLE-HANDEDLY ACTUATABLE SHIELD

RELATED APPLICATIONS

This application is a continuation of Utility application Ser. No. 11/263,025, filed on Oct. 31, 2005 now abandoned.

BACKGROUND OF THE INVENTION

The subject invention relates to single-handedly actuatable shield for hypodermic needles, blood collection needles, catheter needles and other medical implements to help prevent accidental needle sticks.

DESCRIPTION OF THE PRIOR INFORMATION

An accidental needle stick involving a used needle cannula can transmit disease. As a result, most prior art needle cannulas are used with a safety shield for preventing accidental needle sticks.

Most prior art hypodermic needle assemblies have a cap-like safety shield telescoped over the needle cannula prior to use. The proximal portions of the shield may be frictionally retained on a needle hub. The needle assembly is placed in condition for use by merely removing the cap-like safety shield. Re-shielding of the needle after use, using the removable needle shield, is generally discouraged because of the potential for accidental needle sticks.

The prior art has addressed the problem of post-injection unshielded needle cannula by providing sharps collectors and a variety of needle assemblies having self-contained shields which are activatable after injection.

An example of an improved needle shield is taught in U.S. Pat. Nos. 5,348,544; 5,735,827; 5,738,655; and 5,910,130. Such a needle shield has the advantage of being single-handedly activated and while in its collapsed needle exposing position minimizes the amount of projecting structure which can limit the view of the needle cannula or interfere with the injection process.

This shieldable needle assembly includes a needle guard which is slidably movable along the needle cannula from a proximal position substantially adjacent to a hub to a distal position surrounding the distal end of the needle cannula. The needle assembly further includes a hinged arm for initiating movement of the needle guard and for controlling the amount of movement of the needle guard along the needle cannula. The hinged arm assembly includes a proximal segment hingedly connected to the needle hub and a distal segment articulated to portions of the proximal segment remote from the hub and to the needle guard. In the collapsed needle exposing position the hinged arm is folded upon itself and is substantially adjacent to the hub. However, distally directed forces may be exerted on the hinged arm to urge the hinged arm assembly into an extended condition in which its segments are substantially linearly arrayed and generally parallel to the needle cannula. The dimensions of the segments of the hinged arm assembly are selected to permit distal portions of the needle guard to move beyond the distal end of the needle cannula and prevent proximal portions of the needle guard from moving beyond the end of the needle cannula. Movement of the hinged arm assembly from the collapsed condition to the extended condition may be facilitated by an energy source such as a spring intended to propel the needle guard in a distal direction toward the needle shielding position.

There is still a need for an improved single-handedly actuated shield for needles that includes structure for resisting excessive forces improperly applied to the needle assembly after use which could re-expose the distal end of the needle.

SUMMARY OF THE INVENTION

A shieldable needle assembly of the present invention includes a needle cannula having a proximal end and a distal tip. A guard having a proximal end, an opposed distal end and a side wall extending therebetween is slidably movable along the needle cannula from a first position substantially adjacent to the proximal end of the needle cannula to a second position where the distal tip of the needle cannula is intermediate the opposed proximal and distal ends of the guard. A hinged arm having proximal and distal segments articulated to one another through an intermediate hinge is provided for movement of the hinged arm between a first position where the segments are substantially collapsed onto one another and a second position where the segments are extended from one another. The proximal segment of the hinged arm is articulated to a portion of the needle assembly adjacent to the proximal end of the needle. The distal end of the distal segment of the hinged arm is articulated to the guard. The proximal and distal segments of the hinged arm have respective lengths for permitting the guard to move from the first position to the second position on the needle cannula and for preventing the guard from moving distally beyond the second position. An energy storing and releasing structure, such as a spring, is connected to the hinged arm for urging the guard along the needle cannula toward the second needle protecting position. Structure is provided for limiting the reverse rotation of the proximal and distal segments around the intermediate hinge after the guard is in the second position.

Structure for limiting reverse rotation of the intermediate hinge includes a discontinuity on the hinge and an arm discontinuity on either of the proximal and distal segments of the hinged arm. The structure for limiting reverse rotation may include a radial projection on a hinge pin and a discontinuity on the proximal segment wherein the hinge projection snaps substantially irreversibly past the arm discontinuity as the guard moves onto the second position.

Structure may also be provided for limiting continued rotation of the proximal and distal segments around the intermediate hinge after the guard is in its second position. The structure for limiting further continued open rotation may include a contact surface on the proximal end of the distal segment and a contact surface on the distal end of the proximal element. These contact surfaces are positioned to contact each other after the guard is in its second position. The contact surfaces may be on one or more raised projections.

Structure may also be provided to limit upward angular rotation of the guard with respect to the distal element when the guard is in its second position. Such structure may include a stop surface on the guard and a stop surface on the distal end of the distal element to limit upward angular rotation of the guard to an angle equal to or slightly more than the angle between the guard and the distal element when the guard is in its first position.

The proximal end of the guard may further include a proximal wall having an aperture therethrough wherein the needle cannula slidably extends through the aperture of the proximal wall of the guard. The distal end of the guard includes a distal wall having an aperture slidably engaging around the needle cannula when the guard is disposed at its first position. The distal wall is positioned distally beyond the tip of the needle cannula when the guard is in its second position.

The shieldable needle assembly may further include a clip. The clip is configured to cover the tip of the needle cannula when the guard is in the second position on the needle cannula. The clip may be made of metal such as stainless steel or another material highly resistant to puncturing.

The shieldable needle assembly may further include a needle hub securely engaging the proximal end of the needle cannula. The proximal segment of the hinge arm is articulated to the hub.

The shieldable needle assembly may include the hub and proximal segment of the hinge arm being unitary with one another.

The shieldable needle assembly may include spring means which is substantially unbiased when the guard is in the first position. The spring means may be a coil spring. The coil spring may be positioned to extend from a portion of the needle assembly adjacent to the proximal end of the needle cannula to a location on the proximal segment of the hinged arm.

The spring means may include an over-center hinge extending from the proximal segment of the hinged arm and said portion of the needle assembly adjacent to the proximal end of the needle cannula.

The shieldable needle assembly may further include a hypodermic syringe barrel engaging the proximal end of the needle cannula wherein the proximal segment of the hinged arm is articulated to the hypodermic syringe barrel.

DETAILED DESCRIPTION

A shieldable, single-handedly activated, needle assembly in accordance with the subject invention is identified generally by numeral 20 in FIGS. 1-9 Needle assembly 20 includes a needle cannula 21 having a proximal end 22, a distal tip 23 and a lumen 25 extending therethrough. Distal tip 23 in this embodiment includes a bevel 26 aligned at an acute angle to the longitudinal axis of the needle cannula.

Figure 1:
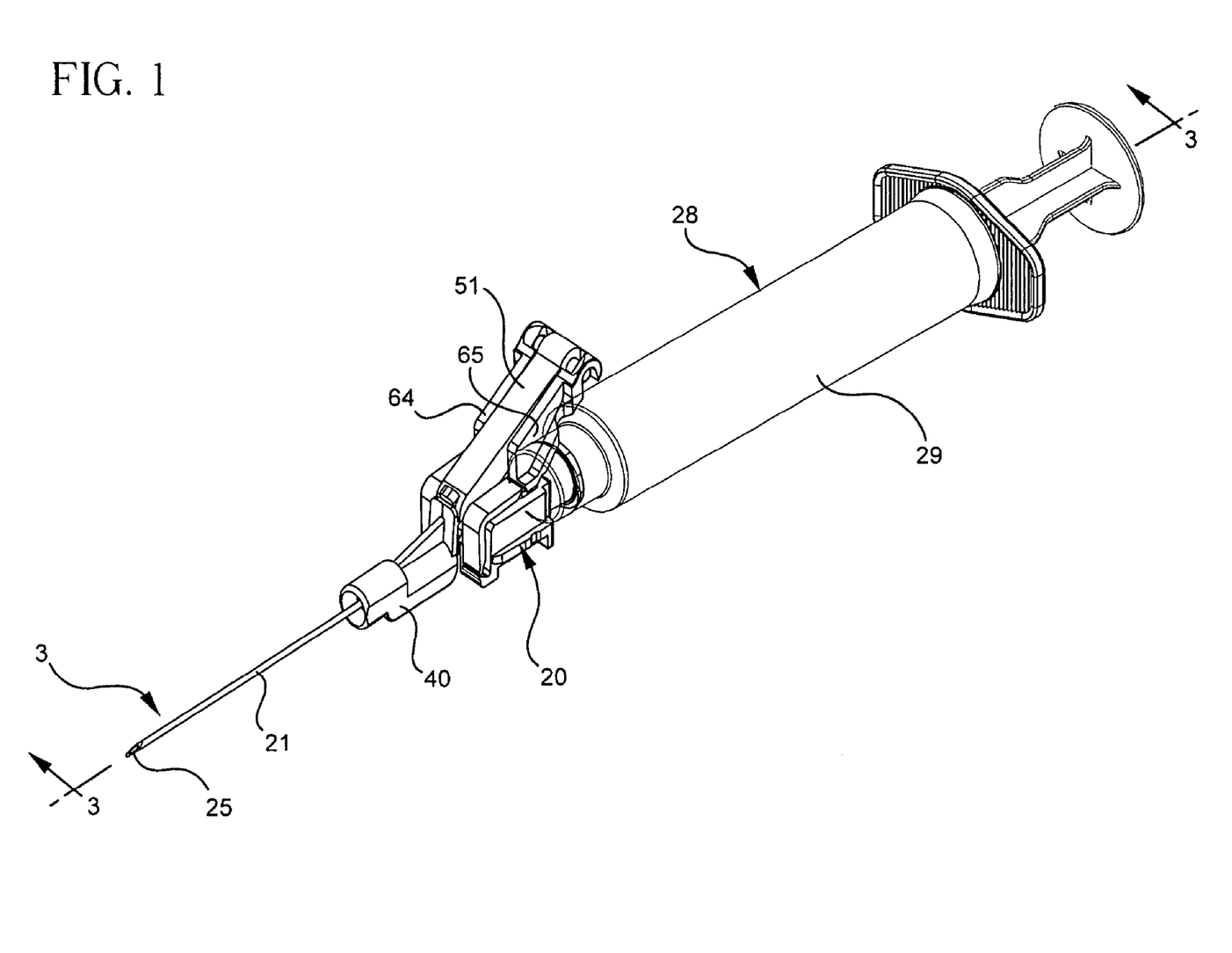
FIG. 1 is a perspective view of a hypodermic syringe having a shieldable needle assembly of the present invention.
Figure 2:
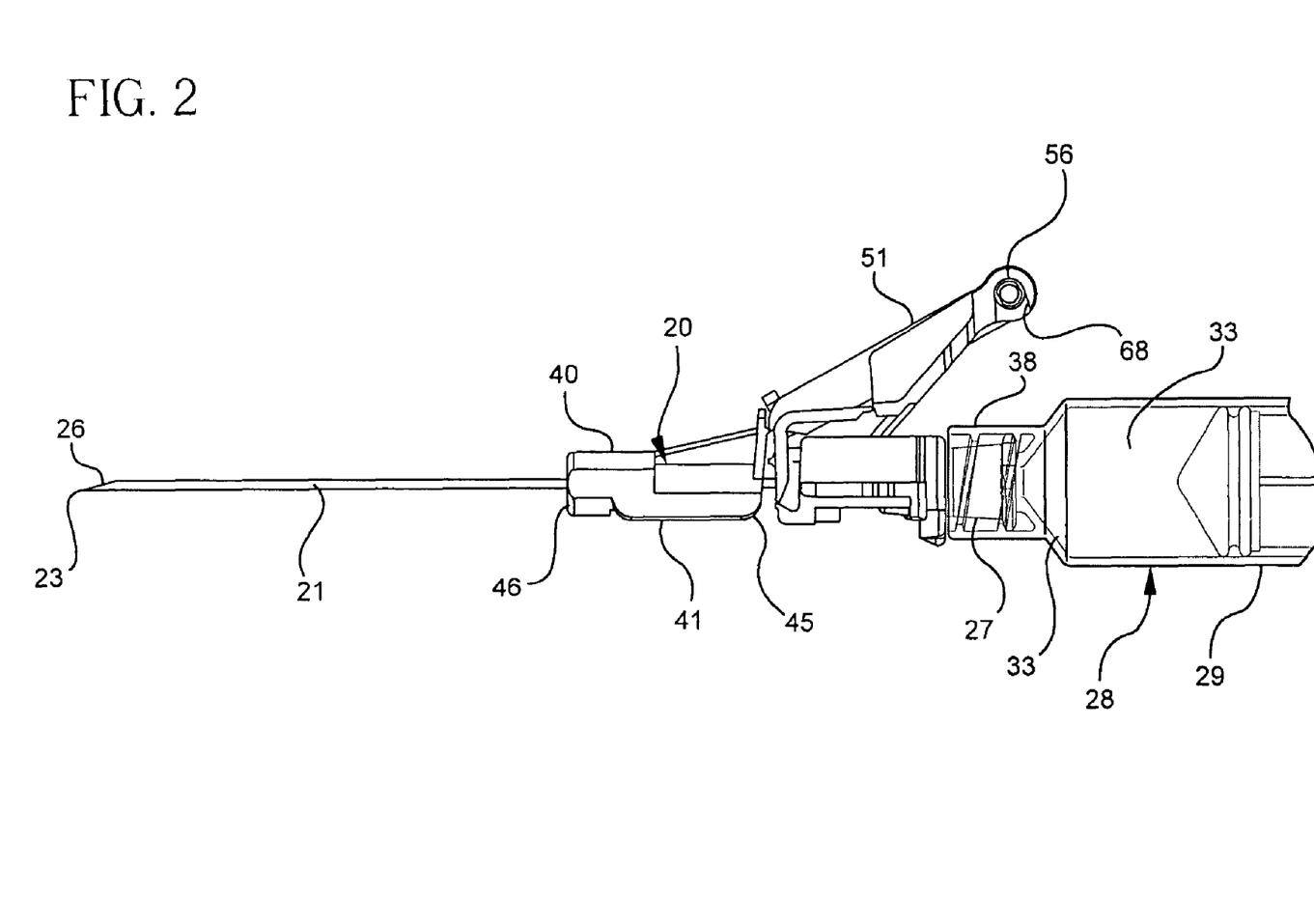
FIG. 2 is a partial side elevational view of the syringe and shieldable needle assembly of FIG. 1.

Needle assembly 20 further includes a needle hub 27 which is securely engaged to proximal end 22 of the needle cannula. Needle assembly 20 may be connected to a fluid transfer device such as hypodermic syringe 28 as shown in FIGS. 1 and 2. The syringe includes a barrel 29 having opposed proximal and distal ends 31 and 32 respectively and a fluid chamber 33 extending therebetween. Proximal end 31 of the syringe barrel is open and slidably receives a plunger 34. Distal end 32 of the syringe barrel includes an elongate tip 35 having a passageway 37 extending therethrough. Distal end 32 of the syringe barrel preferably includes a luer collar 38 concentrically surrounding tip 35. The luer collar includes an internal thread which may be engaged by the needle hub.

Tip 23 of needle cannula 21 may become contaminated after being used to deliver medication to a patient. Needle assembly 20 enables unimpeded use of the needle cannula and hypodermic syringe and insures effective shielding of tip 23 of the needle cannula immediately after withdrawal from a patient, as explained herein.

The preferred shieldable needle assembly 20 includes a guard 40 which includes a cap portion 41 and a clip 43. Cap 41 is preferably molded from a thermoplastic material to include a side wall 44 preferably extending circumferentially through more than 180 degrees, and having opposed proximal and distal ends 45 and 46 respectively. Side wall 46 is preferably longer than bevel tip 18 of the needle cannula. Cap 41 further includes an end wall 47 extending across distal end 46 of side wall 44. End wall 47 includes an aperture 49 which is slidable along needle cannula 21.

Figure 7:
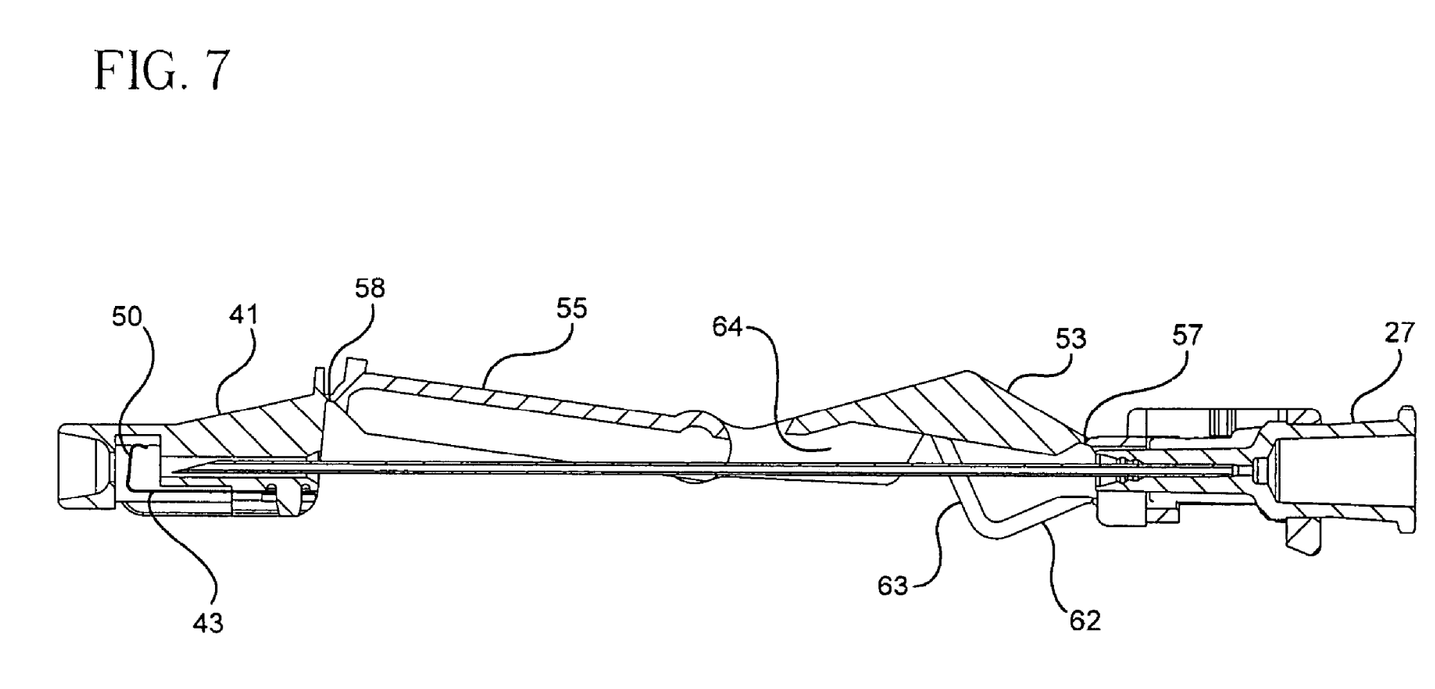
FIG. 7 is a cross-sectional view of the needle shield assembly of FIG. 5 taken along line 7-7.

Clip 43 of needle guard 40 is retained between needle cannula 21 and cap 41. Clip 43 includes a distal wall 50 that is configured to be biased against needle cannula 21. However, sufficient distal movement of cap 41 will cause distal wall 50 of the clip to pass beyond tip 23 of the needle cannula. Distal wall 50 of the clip will then be biased over tip 23 as illustrated in FIG. 7. Clip 43 is preferably made of metal such as stainless steel or other material exhibiting good penetration resistance. Clip 43 provides more protection against penetration by tip 23 than could be provided by a plastic cap alone. Additionally, a clip made of metal or other puncture-resistant material enables the plastic of the shieldable needle assembly to be selected for its resiliency and other performance characteristics with less concern for the ability of the plastic to resist needle punctures.

Needle assembly 20 further includes a hinged arm assembly 51 having a proximal segment 53 and a distal segment 55 which are articulated to one another at hinge pins 56. Proximal segment 53 of hinged arm assembly 51 is articulated to hub 27 at a proximal hinge 57. Distal segment 55 of the hinged arm assembly is articulated to cap 41 at a distal hinge 58. Hub 27, cap 41 and hinged arm 51 may be unitary with one another. However, in the preferred embodiment shown herein proximal and distal segments 53 and 55 are snapped into engagement with one another through hinge pins 56. Proximal hinge 57 between hub 27 and proximal segment 53 of the hinged arm assembly is preferably an over-center spring hinge. More particularly, hinge 57 includes a substantially non-biasing hinge member 59 and spring element 61. Non-biasing hinge member 59 defines the rotational path about which the proximal segment of the hinged arm assembly will rotate relative to the needle hub. Spring element 61 in this preferred embodiment includes first and second segments 62 and 63 which are substantially orthogonally aligned to one another in an unbiased condition, as shown in FIG. 2. However, first and second segments 62 and 63 of the spring element can be resiliently deflected from the unbiased angle alignment into a more linear alignment.

Figure 4:
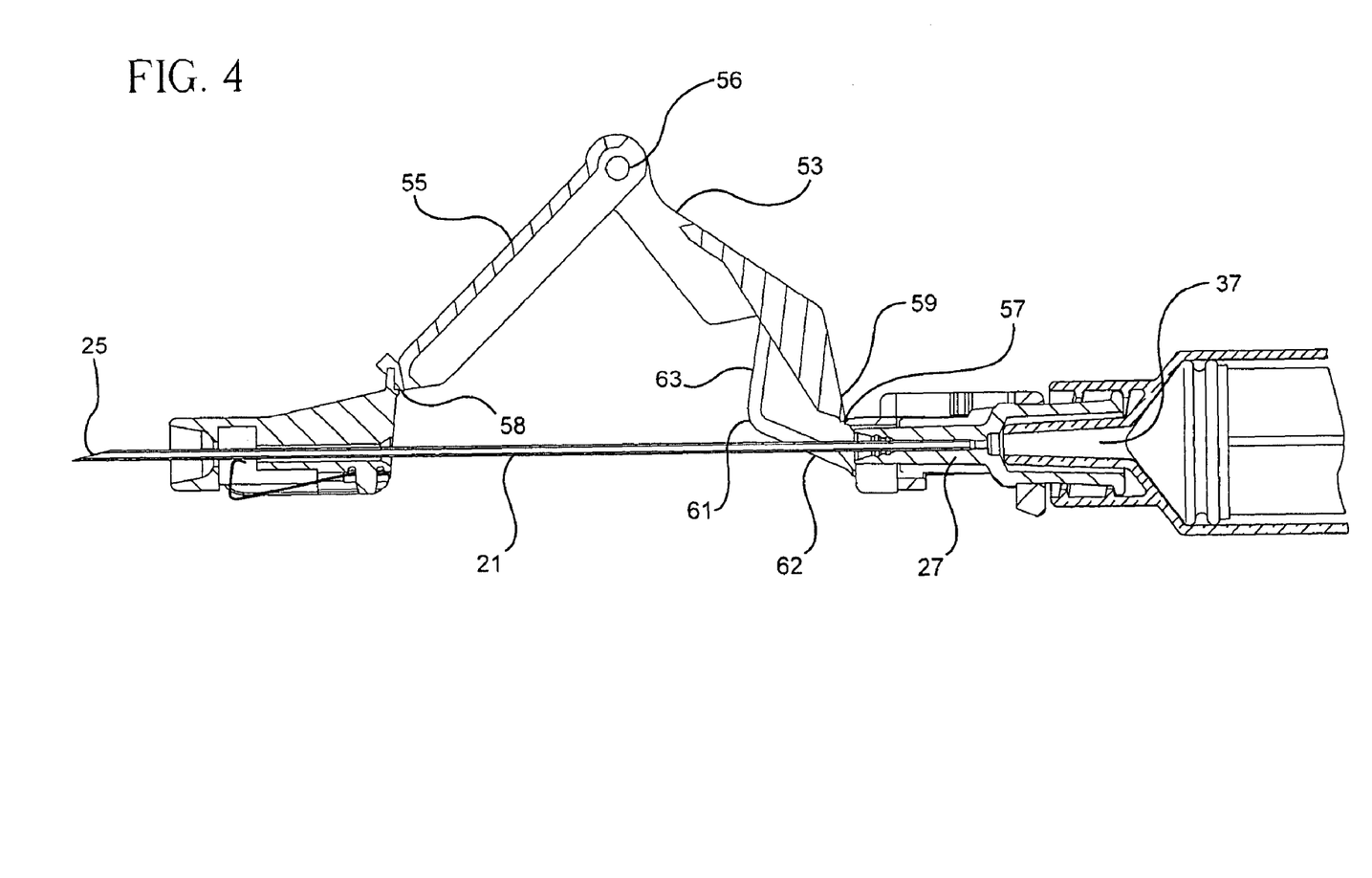
FIG. 4 is a cross-sectional view similar to FIG. 3 but showing the shield in a partially extended position.

Rotation of proximal segment 53 of the hinged arm assembly from the alignment shown in FIG. 2 toward the alignment shown in FIG. 4 will cause segments 62 and 63 to leave spring element 61 to be deflected from the approximate right angle condition shown in FIG. 2 toward the more linear orientation as shown in FIG. 4. The user of syringe 28 and needle assembly 20 must manually overcome the forces attributable to the resiliency of spring element 61 to move proximal segment 53 of the hinged arm assembly from the orientation of FIG. 2 to the orientation of FIG. 4. The resiliency inherent in spring element 61 will urge the spring hinges back toward an undeflected approximate right angle condition. This resiliency will effectively propel proximal segment 53 of the hinged arm assembly from orientation illustrated in FIG. 4 to that toward the orientation illustrated in FIGS. 6 and 7 with proximal segment 53 being adjacent to needle cannula 21. Simultaneously, distal segment 55 will rotate into substantially parallel alignment with the needle cannula and guard 40 will slide distally toward tip 23 of the needle cannula.

The self-propelling feature enabled by hinge 57 is desirable and facilitates one-handed actuation of the needle guard. Equally important, is the fact that hinge 57 is in a stable condition in its FIG. 2 orientation with substantially no stored energy exerting pressure on the plastic components of the shieldable needle assembly. Stored energy acting on plastic can affect the reliability and performance of the part. In this instance, however, the stored energy is accumulated only after proximal segment 53 of hinged arm assembly 51 is moved from the stable position of FIG. 2 into the FIG. 4 orientation. The accumulated energy then performs work for the user by moving the hinged arm assembly toward its FIGS. 6 and 7 orientation. Hinge 57 will again be stable with substantially no stored energy FIGS. 6 and 7 orientation where the needle cannula is safely shielded. Another feature of the present invention is that the spring element while in the orientation of FIGS. 1 and 2 will resist accidental or inadvertent pressure which would tend to force the guard toward the second position where the clip covers the end of the needle.

Proximal segment 63 of hinged arm assembly 51 includes a pair of parallel spaced-apart arms 64 and 65 which terminate at the linear bearing slots 67 and 68 respectively. The bearing slots are dimensioned to receive hinge pins 56 which in this embodiment are unitarily molded as part of distal segment 55 of the hinged arm assembly.

Figure 3:
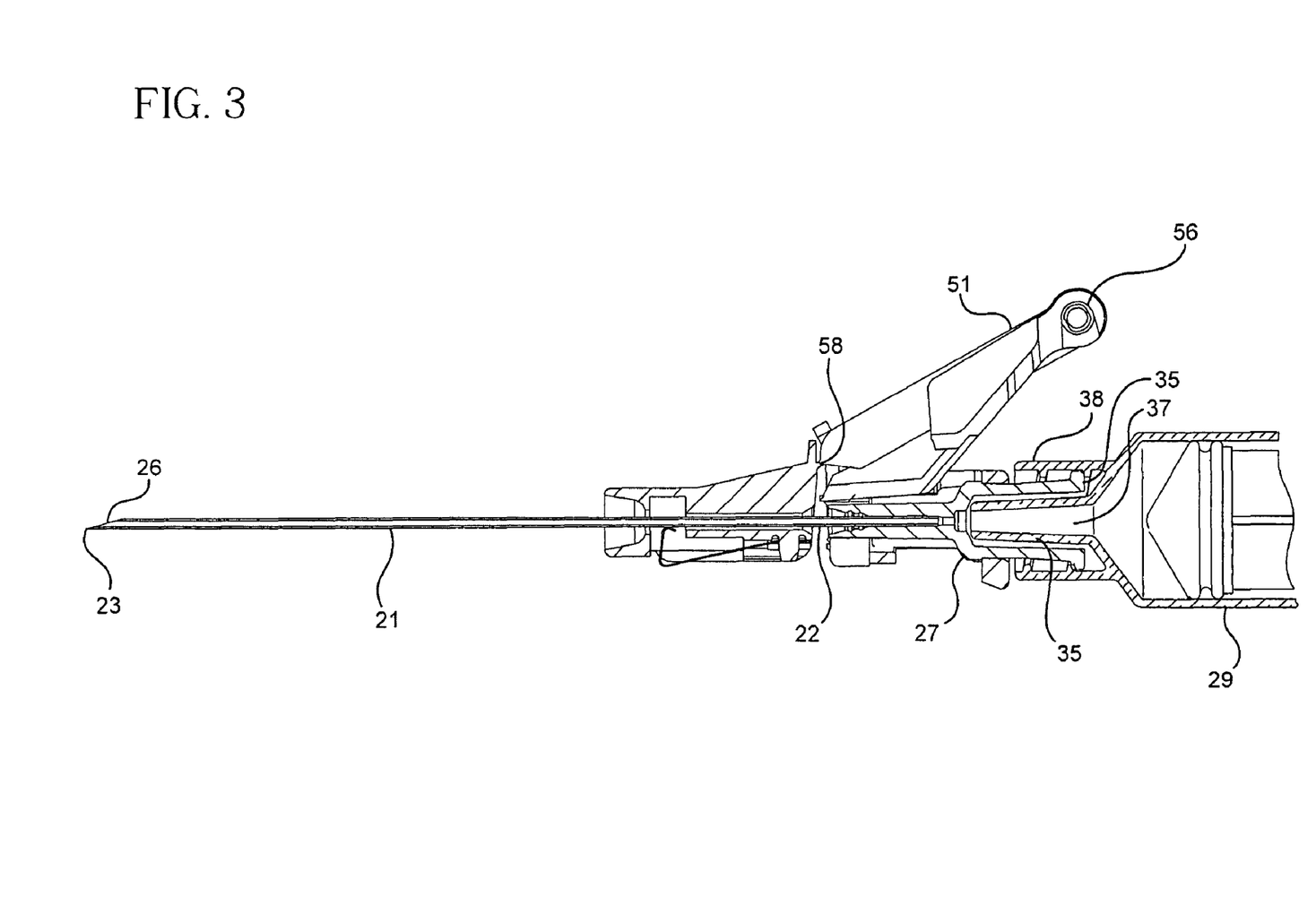
FIG. 3 is a cross-sectional view of the shieldable needle assembly of FIG. 1 taken along line 3-3.

As shown in FIGS. 1-3, distal segment 55 can be articulated around hinge pins 56 into a collapsed position. The relatively small dimensions of each segment 52 and 53, and the nesting of those segments in a collapsed condition substantially eliminates visual or physical obstruction of the cannula by the hinged arm assembly. The hinged arm assembly is preferably aligned to define a plane which passes symmetrically through the bevel 26 on the tip of the needle cannula. Thus, the hinged arm assembly can be used as a guide to achieve a desired alignment of the bevel prior to insertion of the needle into a vein in the patient. If it is desirable to have the bevel tip facing upwardly, the user of the syringe merely orients the collapsed hinged arm assembly of FIGS. 1-3 to point upwardly. The hinged arm assembly can also facilitate the initial threaded engagement of the needle hub into the luer collar 38 of syringe barrel 29.

After using syringe 28, proximal and distal segments 53 and 55 of the hinged arm assembly can be articulated about hinges 56, 57 and 59 toward an extended position, with guard 40 slidably telescoping along the needle cannula and away from the needle hub.

Figure 5:
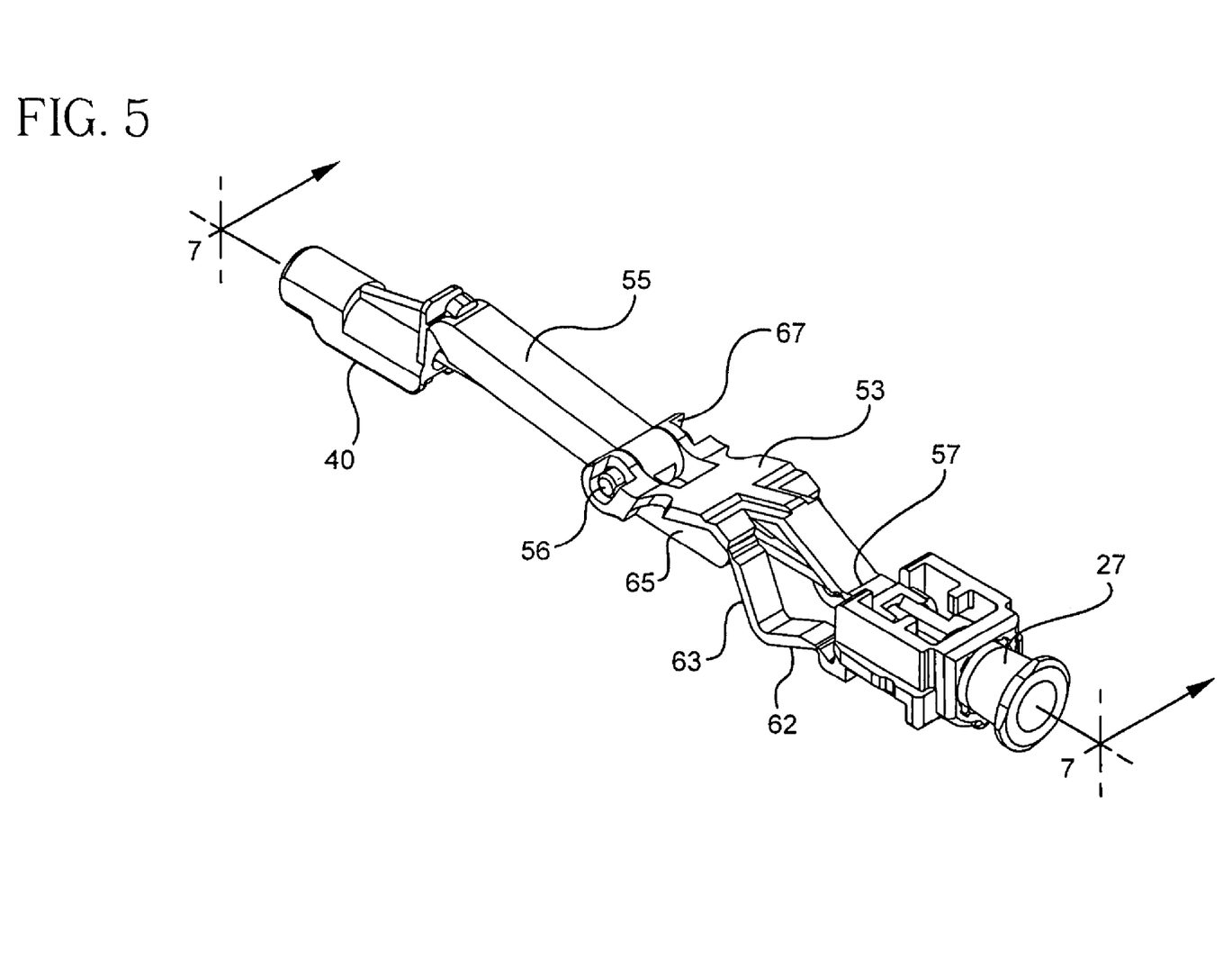
FIG. 5 is a perspective view of the shieldable needle assembly showing the needle shield in its fully extended condition shielding the tip of the needle cannula.
Figure 6:
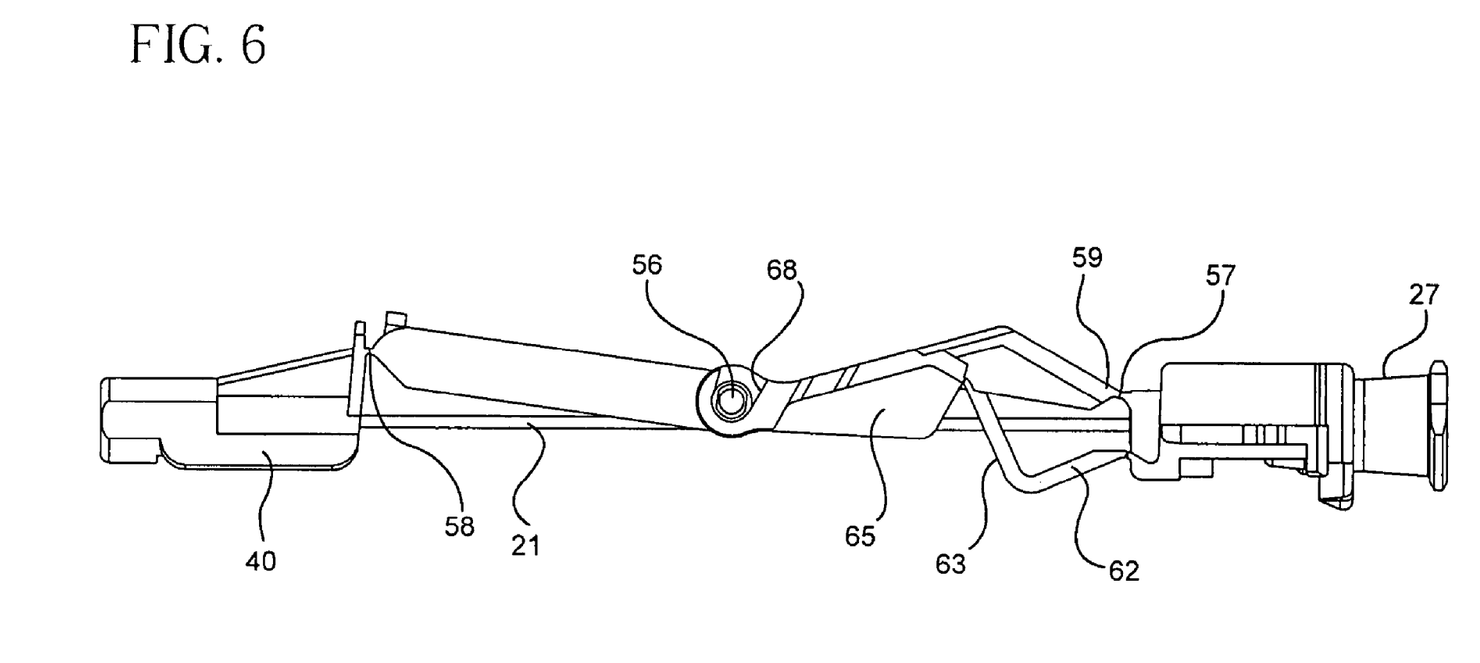
FIG. 6 is a side-elevational view of the needle assembly of FIG. 5.

This extension of the hinged arm assembly from the collapsed condition of FIGS. 1-3 to the extended position of FIGS. 5-7 can be generated entirely from locations proximally on needle cannula 21. More particularly, proximal member 53 of the hinged arm assembly extends radially outwardly from the needle cannula sufficiently to define a proximally-facing actuation surface extending transversely from the syringe barrel. Thus, distally directed pressure by a finger on the hand engaging the syringe barrel will urge the hinged arm assembly from its collapsed condition toward its extended condition and thereby urge guard 40 toward distal tip 21 of the needle cannula.

Proximal and distal segments of the hinged arm assembly are dimensioned to permit end wall 47 of cap 41 and distal wall 50 of clip 43 to pass distally beyond tip 23 of the needle cannula as shown in FIG. 7. However, the respective length of the proximal and distal segments 53 and 55 of the hinged arm assembly prevent complete separation of the guard from the needle cannula. Additionally, the configuration of clip 43 causes the needle cannula to be biasingly trapped by clip 43.

Figure 8:
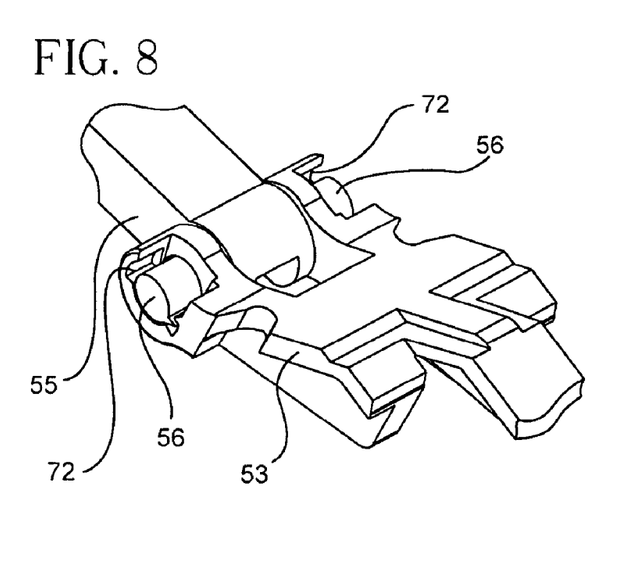
FIG. 8 is an enlarged perspective view of the intermediate hinge of the needle assembly of FIG. 6.
Figure 9:
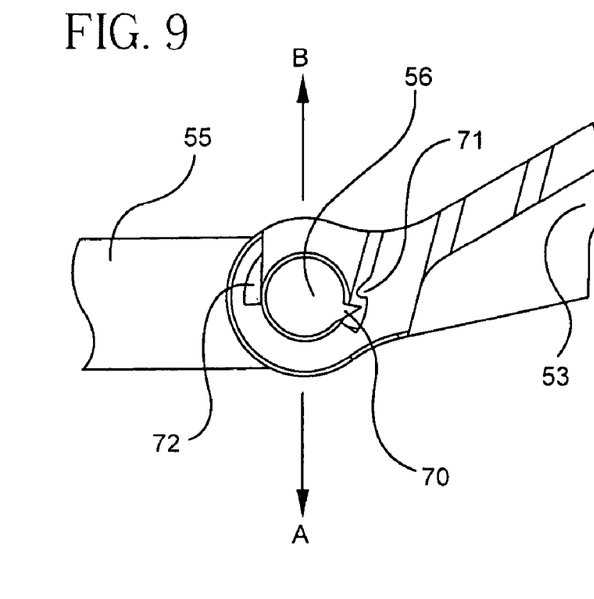
FIG. 9 is a side elevational view of the intermediate hinge of FIG. 8.

After the hinged arm assembly is extended to the position illustrated in FIGS. 5-7 needle assembly is not reusable and should be disposed of in a safe manner. The normal forces associated with safe disposal of needles and syringes will not re-expose the needle tip. A person applying excessive bending forces to the needle assembly, after use, in an attempt to improperly re-expose the needle tip by extending the guard past the end of the needle tip would likely bend the needle cannula and make it unsuitable for use. In order to make the hinged arm assembly of the present invention more rigid and resistant to unauthorized excessive force to improperly reuse the needle, additional features are provided to prevent excessive additional rotation of the hinged element after the tip of the needle cannula is shielded. In particular, structure is provided for limiting reverse rotation of the proximal and distal segments of the hinged arm assembly around the intermediate hinge after the guard is in the needle protecting position. Referring to FIGS. 8-9, the preferred structure for limiting reverse rotation of the intermediate hinge includes a discontinuity on one or both hinge pins 56 for engaging a discontinuity on either the proximal or the distal segment of the hinge arm depending on which arm the hinge pin is attached to. In this preferred embodiment, hinge pin is attached to the proximal end of the distal segment and the discontinuity is contained in the distal end of the proximal segment. In particular, radial projection 70 is positioned on hinge pins 56 and is positioned to snap over projections 71 in bearing slots 67 and 68. Radial projection 70 and projection 71 are shaped to pass over each other with minimal resistance as the hinge moves in direction A, transverse to the needle cannula while being shaped to strongly resist reverse rotation of the intermediate hinge, i.e., moving the hinge in direction B transverse to the needle cannula. This feature is especially useful if unauthorized reuse is attempted by disabling or removing the metal clip to re-expose the needle through the distal end of the guard.

A recess may be positioned in one or both bearing slots to contain the radial projection or projections while the hinged arm is in its first needle exposing position wherein segments 53 and 55 are substantially collapsed on one another. In this embodiment there is a recess 72 in each of the bearing slots 67 and 68. Radial projections 70 on hinge pins 56 are positioned in recesses 72 when the hinged arm is in its first needle exposing position. In this position the radial projections are in a relaxed, stress-free, state and have little or no contact with any portion of the bearing slots 67 and 68. This relationship of the projections 70 and recesses 72 can help stabilize the hinged arm assembly and help hold it in its first needle expositing position. In this case, initial movement of the hinged arm assembly toward its second needle protecting position will require an additional force to snap the projections 70 out of the recesses 72.

Figure 10:
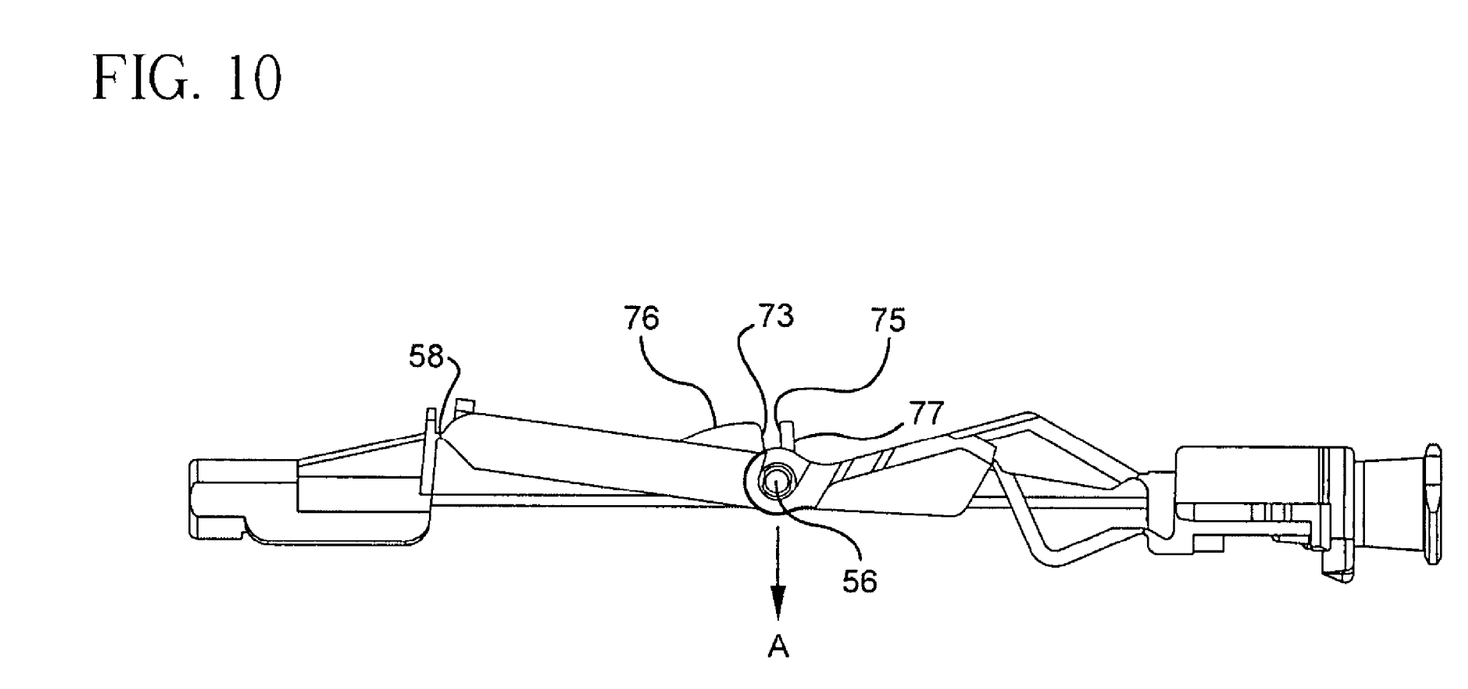
FIG. 10 is a side elevational view of the needle shield assembly showing structure to help prevent further inward rotation of the intermediate hinge after the needle tip has been shielded.
Figures 11, 12:
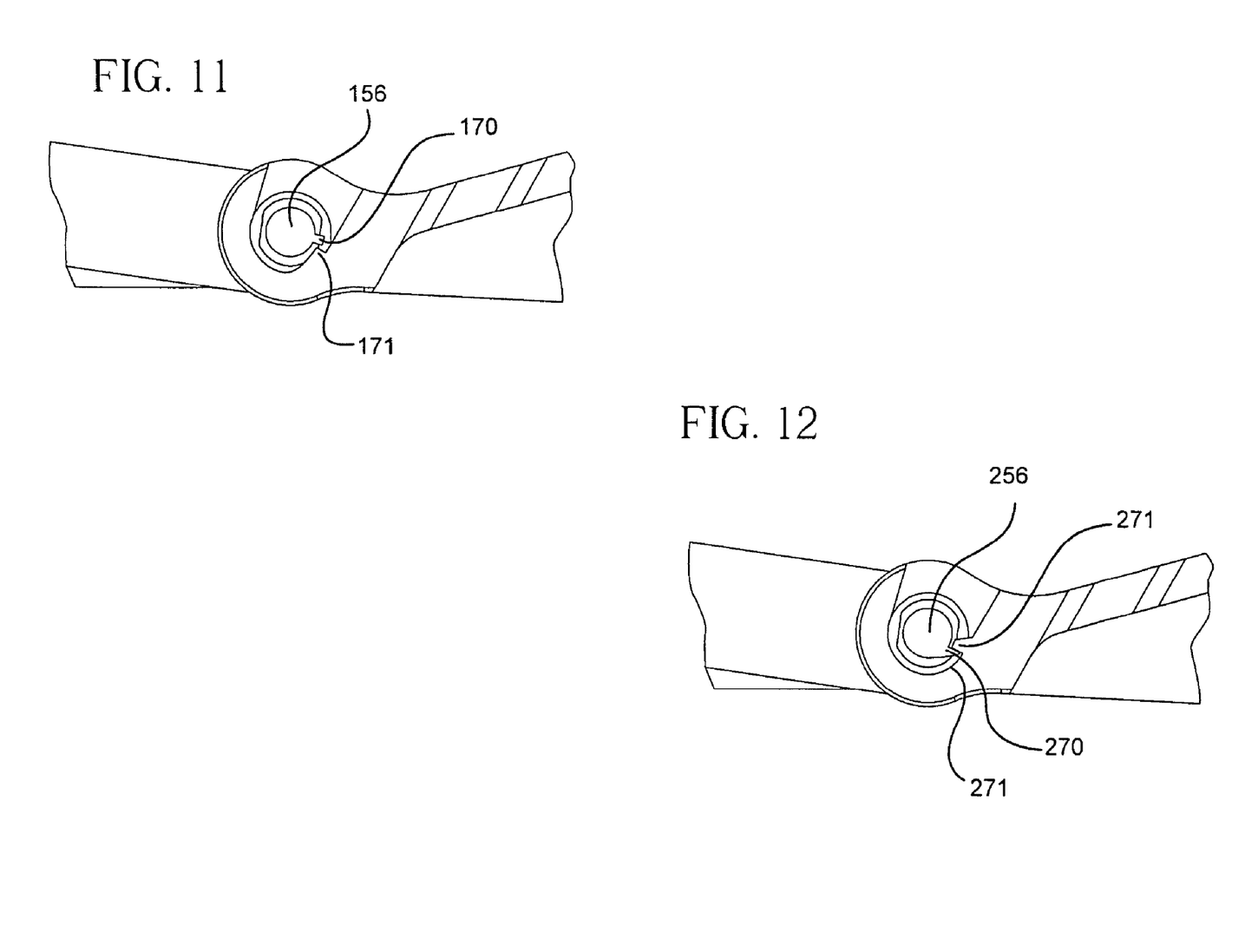
FIG. 11 illustrates another structure to prevent further inward rotation of the intermediate hinge.
FIG. 12 is still another structure for preventing further inward rotation of intermediate hinge.

Referring to FIGS. 10-12, it is also desirable to provide structure for limiting the continued opening rotation of the proximal and distal segments around the intermediate hinge after the guard is in its second needle protecting position. To limit continued opening rotation of the needle assembly in the alternative embodiment of FIG. 10 includes contact surface 73 on the proximal end of distal segment 55 and a contact surface 75 on the distal end of proximal segment 53. The contact surfaces are positioned to contact each other after said guard is in its second needle protecting position to prevent further continued rotation of the proximal and distal segments of the hinged arm assembly around the intermediate hinge. In this embodiment, both contact surfaces take the form of radial projections 76 and 77 respectively and contact each other as the hinge pins move in direction A.

FIG. 11 illustrates another alternative structure for limiting continued opening rotation of the proximal and distal segments around the intermediate hinge after the guard is in its needle protecting position. In this embodiment, hinge pins 156 include radial lugs 170 and ledges 171 in the bearing slots. The ledges and the radial lugs are positioned to abruptly resist further opening rotation of the intermediate hinge after the guard is in its needle protecting position.

FIG. 12 illustrates another alternative structure for limiting continued open rotation of the intermediate hinge. In this embodiment, hinge pins 256 each contain a radial projection 270 which is similar to the radial projection 70 illustrated in FIGS. 8 and 9. However, in this embodiment, the bearing slots include a resisting surface 271 which resists further opening rotation of the intermediate hinge. This embodiment may also include an inwardly-directed projection on each of the bearing slots to also resist reverse rotation of the intermediate hinge after the needle guard is in its second needle protecting position.

Figure 13:
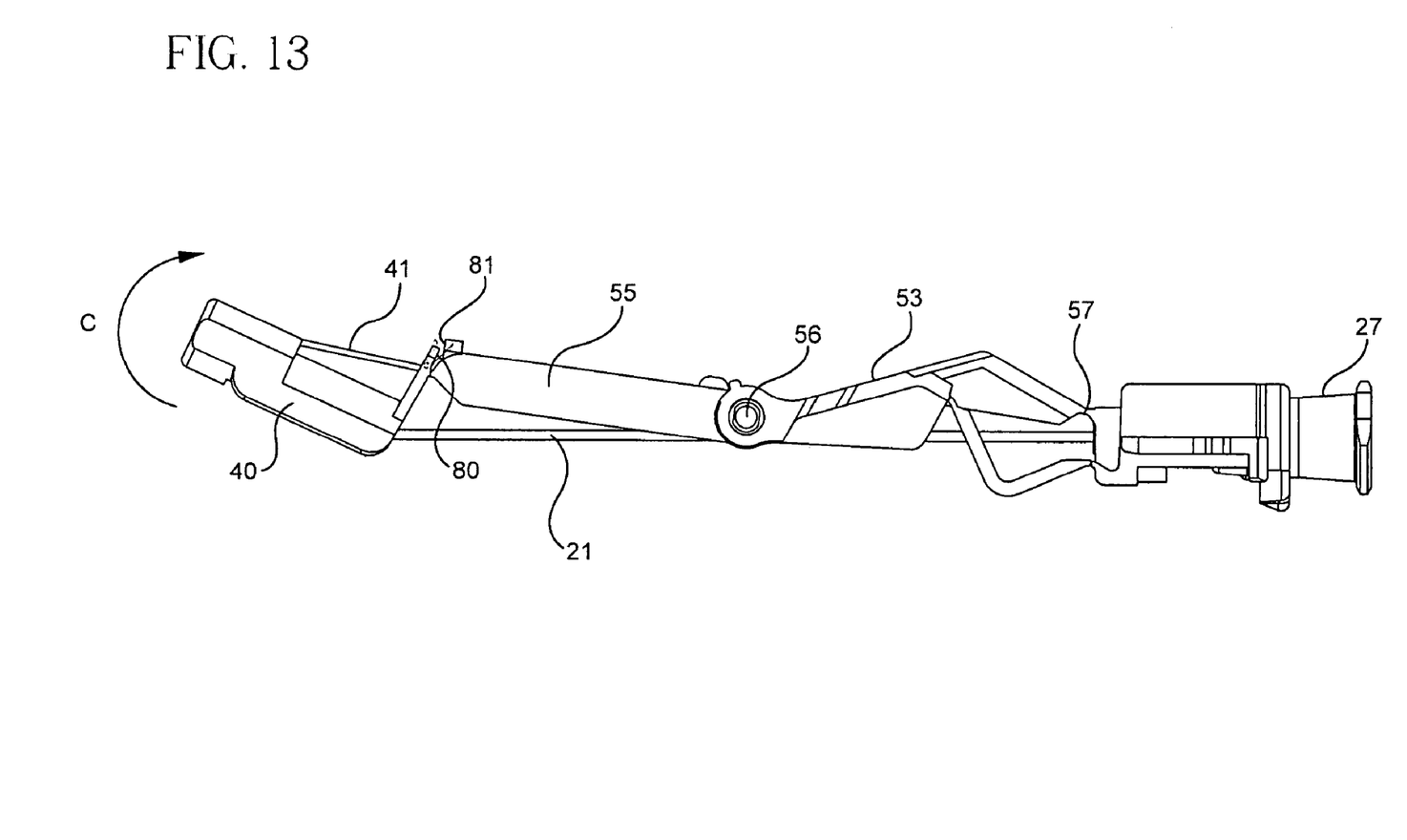
FIG. 13 is a side elevation view of the needle shield assembly of the present invention showing structure for preventing upward rotation of the needle guard after it is in its needle shielding position.

FIG. 13 illustrates another alternative embodiment of the present invention. In this embodiment a stop surface 80 on cap 41 of guard 40, and a stop surface 81 on the distal end of distal segment 55 are positioned to limit further angular upward rotation (indicated by letter C). This feature is a further safeguard to prevent improper forceful re-exposure of the needle tip. It should be noted that the stop surfaces 80 and 81 have to be positioned as far apart as necessary for the hinged assembly to collapse upon itself in the needle expositing position.

Figure 14:
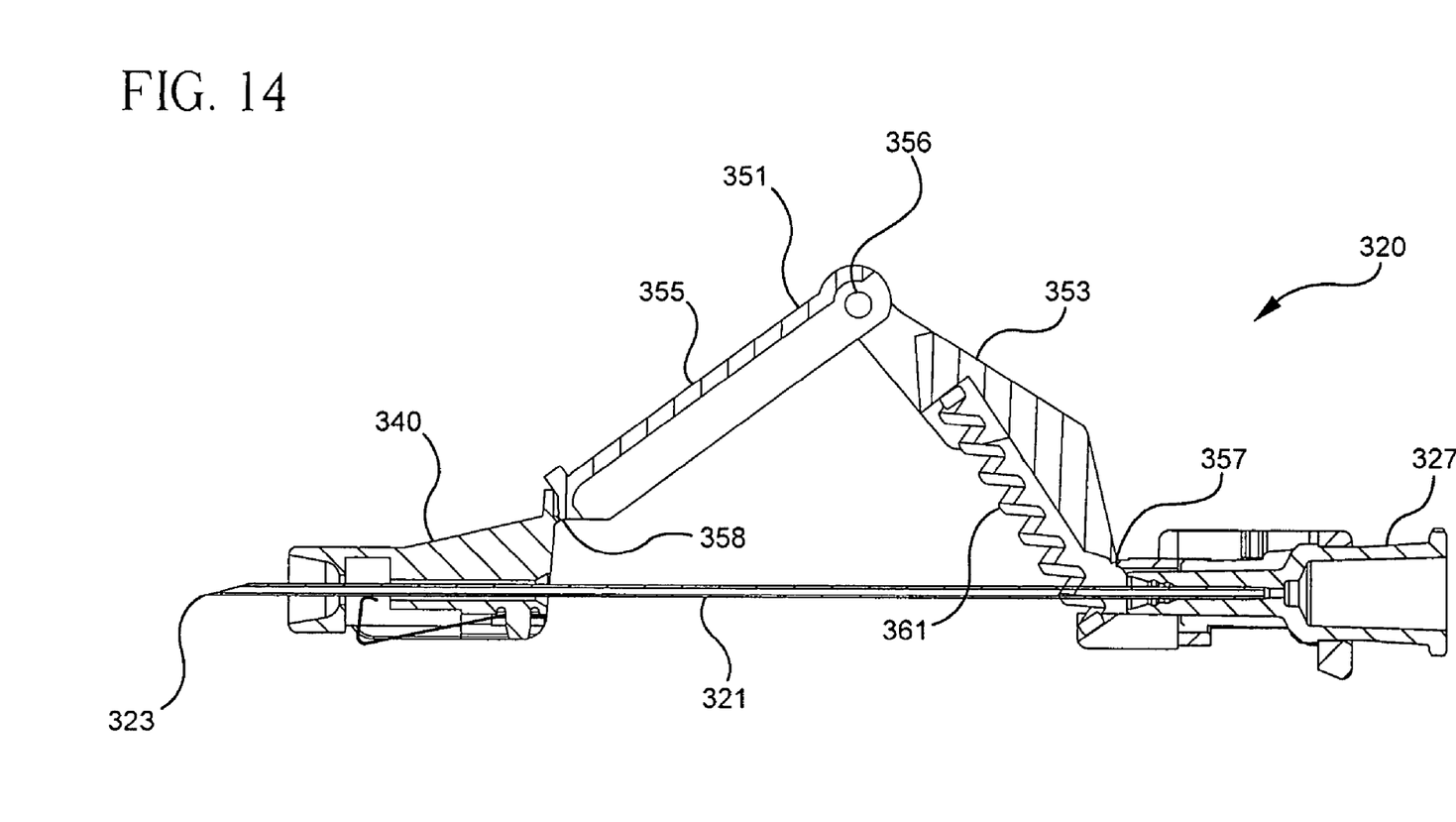
FIG. 14 is a cross-sectional view similar to FIG. 4 showing an alternative embodiment wherein the spring element is a coil spring.

FIG. 14 illustrates an alternative embodiment wherein the spring element is a coil spring. This embodiment functions substantially the same as the embodiments of FIGS. 1-7. In this embodiment needle assembly 320 includes a needle cannula 321 and a guard 340 slidably movable along the needle cannula from a first position substantially adjacent to a hub 327 to a second position wherein a distal tip of the needle cannula is within a guard. Like the embodiment of FIGS. 1-7, needle assembly 320 has a hinged arm 351 having a proximal segment 353 and a distal segment 355 articulated to one another through hinge 356 for movement between the first and second position. The proximal segment of the hinged arm is articulated to the hub through proximal hinge 357 and the distal end of the distal segment is articulated to the guard through hinge 358. A coil spring 361 preferably extends from the needle hub to proximal segment 353. Coil spring 361 is stretched by moving hinged arm 353 from the needle exposing position where the guard that is adjacent to the hub toward the needle protecting position as illustrated in FIG. 14. To achieve orientation of FIG. 14 the coil spring is stretched. The energized coil spring contracts urging the needle guard distally toward the tip of the needle cannula substantially as explained in the preceding embodiment of FIGS. 1-7.

The spring element of the present invention can comprise a variety of materials and configurations of energy storing and releasing elements. The spring element material may include elastomeric materials, thermoplastic materials and/or metal and the like. Spring element configurations may vary widely from straight elastomeric elements to specifically shaped coil springs, cantilever springs, and combinations thereof formed for the specific application. All of these spring elements are within the purview of the present invention with the spring element of FIGS. 1-7 and the spring element of FIG. 14 being merely representative of these many possibilities.

What is claimed is:

1. A shieldable needle assembly comprising:
    a needle cannula having a proximal end and a distal tip;
    a guard having a proximal end, an opposed distal end and a side wall extending therebetween, said guard being slidably movable along said needle cannula from a first position substantially adjacent said proximal end of said needle cannula to a second position where said distal tip of said needle cannula is intermediate said opposed proximal and distal ends of said guard;
    a hinged arm having proximal and distal segments articulated to one another through a hinge, for movement between a first position where said segments are substantially collapsed onto one another and a second position where said segments are extended from one another, said proximal segment of said hinged arm being articulated to a portion of said needle assembly adjacent said proximal end of said needle cannula, said distal segment of said hinged arm being articulated to said guard, said proximal and distal segments of said hinged arm having respective lengths for permitting said guard to move from said first position to said second position on said needle cannula, and for preventing said guard from moving distally beyond said second position;
    a spring connected to said hinged arm and said guard; and
    said hinge having a pin with a discontinuity that cooperatively engages a slot around a part of said pin when said guard is in said second position to resist further rotation of said hinge and an arm discontinuity on either of said proximal and distal segments of said hinged arm.

2. The shieldable needle assembly of claim 1 where said discontinuity on said hinge is a radial projection, and said arm discontinuity is a discontinuity on said proximal segment wherein said hinge projection snaps irreversibly past said arm discontinuity as said guard moves into said second position.

3. The shieldable needle assembly of claim 2 wherein a recess in said arm contains said radial projection when said guard is in its first position.

4. The shieldable needle assembly of claim 3 wherein said radial projection and said recess are configured to help retain said guard in said first position and require an additional force to dislodge said radial projection from said recess to move said guard toward said second position.

5. The shieldable needle assembly of claim 1 further comprising a contact surface on said proximal end of said distal segment and a contact surface on said distal end of said proximal element, said contact surfaces being positioned to contact each other after said guard is in said second position.

6. The shieldable needle assembly of claim 5 wherein said contact surface on said proximal end of said distal element includes a raised projection.

7. The shieldable needle assembly of claim 1 further including a stop surface on said guard and a stop surface on said distal end of said distal element positioned to limit upward angular rotation of said guard with respect to said distal element to an angle equal to or slightly more than the angle between said guard and said distal element when said guard is in said first position.

8. The shieldable needle assembly of claim 1, wherein said proximal end of said guard comprises a proximal wall having an aperture therethrough, and wherein said needle cannula slidably extends through said aperture of said proximal wall of said guard.

9. The shieldable needle assembly of claim 1, wherein said distal end of said guard comprises a distal end wall having an aperture slidably engaged around said needle cannula when said guard is disposed at said first position, said distal end wall being distally beyond said tip of said needle cannula when said guard is in said second position.

10. The shieldable needle assembly of claim 1, wherein said guard includes a clip, said clip being configured to cover said tip when said guard is in said second position on said needle cannula.

11. The shieldable needle assembly of claim 1, further comprising a needle hub securely engaging said proximal end of said needle cannula, said proximal segment of said hinged arm being articulated to said hub.

12. The shieldable needle assembly of claim 11, wherein said hub and said proximal segment of said hinged arm are unitary with one another.

13. The shieldable needle assembly of claim 1, wherein said spring means is substantially unbiased when said guard is in said first position.

14. The shieldable needle assembly of claim 1, wherein said spring means is a coil spring.

15. The shieldable needle assembly of claim 14, wherein said coil spring extends from a portion of said needle assembly adjacent said proximal end of said needle cannula to a location on said proximal segment of said hinged arm.

16. The shieldable needle assembly of claim 1, wherein said spring means comprises an over-center hinge extending unitarily from said proximal segment of said hinged arm and said portion of said needle assembly adjacent said proximal end of said needle cannula.

17. The shieldable needle assembly of claim 1, further comprising a hypodermic syringe barrel engaging said proximal end of said needle cannula, said proximal segment of said hinged arm being articulated to said hypodermic syringe barrel.

18. The shieldable needle assembly of claim 10 wherein said clip is made of metal.

19. A shieldable needle assembly comprising:
   a needle cannula having a proximal end and a distal tip;
   a guard having a proximal end, an opposed distal end and a side wall extending therebetween, said guard being slidably movable along said needle cannula from a first position substantially adjacent said proximal end of said needle cannula to a second position where said distal tip of said needle cannula is intermediate said opposed proximal and distal ends of said guard;
   a hinged arm having proximal and distal segments articulated to one another through a hinge, for movement between a first position where said segments are substantially collapsed onto one another and a second position where said segments are extended from one another, said proximal segment of said hinged arm being articulated to a portion of said needle assembly adjacent said proximal end of said needle cannula, said distal segment of said hinged arm being articulated to said guard, said proximal and distal segments of said hinged arm having respective lengths for permitting said guard to move from said first position to said second position on said needle cannula, and for preventing said guard from moving distally beyond said second position;
   a spring connected to said hinged arm and said guard; and
   a first contact surface on a first projection extending from an end of said distal segment of said hinged arm near said hinge, said first contact surface facing away from said guard when the guard is in said second position and a second contact surface on a second projection extending from an end of said proximal segment of said hinged arm near said hinge, said second contact surface facing said guard when said guard is in said second position, said first and second contact surfaces being positioned to contact each other after said guard is in said second position, wherein said first projection and said second projection do not overlap each other when said guard is in said second position.

20. The shieldable needle assembly of claim 19, wherein said guard includes a clip, said clip having a distal wall biased against said distal tip of needle cannula said guard is in said second position on said needle cannula.

21. The shieldable needle assembly of claim 19 wherein said contact surface on said proximal end of said distal element includes a raised projection.

22. The shieldable needle assembly of claim 19 further comprising a discontinuity on said hinge and an arm discontinuity on either of said proximal and distal segments of said hinged arm.

23. The shieldable needle assembly of claim 22 where said discontinuity on said hinge is a radial projection, and said arm discontinuity is a discontinuity on said proximal segment wherein said hinge projection snaps irreversibly past said arm discontinuity, as said guard moves into said second position.

24. The shieldable needle assembly of claim 19 further including a stop surface on said guard and a stop surface on said distal end of said distal element positioned to limit upward angular rotation of said guard with respect to said distal element to an angle equal to or slightly more than the angle between said guard and said distal element when said guard is in said first position.

25. The shieldable needle assembly of claim 19, further comprising a needle hub securely engaging said proximal end of said needle cannula, said proximal segment of said hinged arm being articulated to said hub.

26. The shieldable needle assembly of claim 25, wherein said hub and said proximal segment of said hinged arm are unitary with one another.

27. The shieldable needle assembly of claim 19, further comprising a hypodermic syringe barrel engaging said proximal end of said needle cannula, said proximal segment of said hinged arm being articulated to said hypodermic syringe barrel.

* * * * *